(12) United States Patent
Vojtasek

(10) Patent No.: US 6,916,311 B2
(45) Date of Patent: Jul. 12, 2005

(54) HYPODERMIC NEEDLE GUARD

(75) Inventor: William J. Vojtasek, Wyomissing, PA (US)

(73) Assignee: Arrow International Investment Corp., Wilmington, DE (US)

( * ) Notice: Subject to any disclaimer, the term of this patent is extended or adjusted under 35 U.S.C. 154(b) by 705 days.

(21) Appl. No.: 09/878,013

(22) Filed: Jun. 8, 2001

(65) Prior Publication Data

US 2001/0027298 A1 Oct. 4, 2001

Related U.S. Application Data

(62) Division of application No. 09/369,866, filed on Aug. 9, 1999, now Pat. No. 6,280,419.

(51) Int. Cl.[7] .................................................. A61M 5/32
(52) U.S. Cl. ....................................................... 604/192
(58) Field of Search ................................. 604/192, 110, 604/198, 263, 187, 162, 163

(56) References Cited

U.S. PATENT DOCUMENTS

| | | |
|---|---|---|
| 4,747,831 A | 5/1988 | Kulli |
| 4,900,307 A | 2/1990 | Kulli |
| 4,929,241 A | 5/1990 | Kulli |
| 4,981,476 A | 1/1991 | Aichlmayr et al. |
| 5,053,017 A | 10/1991 | Chamuel |
| 5,059,180 A | 10/1991 | McLees |
| 5,183,468 A | 2/1993 | McLees |
| 5,217,438 A | 6/1993 | Davis et al. |
| 5,322,517 A | 6/1994 | Sircom et al. |
| 5,328,482 A | 7/1994 | Sircom et al. |
| 5,334,158 A | 8/1994 | McLees |
| 5,344,408 A | 9/1994 | Partika |
| 5,419,766 A | 5/1995 | Chang et al. |
| 5,425,720 A | 6/1995 | Rogalsky et al. |
| 5,447,501 A | 9/1995 | Karlsson et al. |
| 5,458,658 A | 10/1995 | Sircom |
| 5,558,651 A | 9/1996 | Crawford et al. |
| 5,584,809 A | 12/1996 | Gaba |
| 5,584,810 A | 12/1996 | Brimhall |
| 5,584,818 A | 12/1996 | Morrison |
| 5,611,781 A | 3/1997 | Sircom et al. |
| 5,662,610 A | 9/1997 | Sircom |
| 5,738,665 A | 4/1998 | Caizza et al. |
| 5,779,684 A | 7/1998 | Tamaro |
| 6,221,047 B1 | 4/2001 | Greene et al. |
| 6,280,419 B1 * | 8/2001 | Vojtasek ..................... 604/192 |

* cited by examiner

Primary Examiner—Manuel Mendez
(74) Attorney, Agent, or Firm—Amster, Rothstein & Ebenstein LLP

(57) ABSTRACT

A device for inhibiting unintentional contact with the tip of a needle that has a wire guide disposed in a lumen thereof. A housing of the device has an interior cavity. A portion of the needle extends through the cavity and a tip of the needle is located outside of the housing during use of the needle. A pivoting member is located within the cavity and defines a distal opening and a proximal opening which are sized to allow the needle to pass through the openings. When the needle tip is within the cavity and the needle is withdrawn from the distal opening of the pivoting member, a spring or a compressible member cants the pivoting member into locking engagement with the needle to prevent further movement of the needle. Alternatively, a spring is in locking engagement with the needle to prevent its further movement. When the pivoting member is canted about the needle, a slot of the pivoting member is generally aligned with the tip of the needle so that the wire guide can extend through the slot while further forward movement of the needle through the slot is prevented.

19 Claims, 9 Drawing Sheets

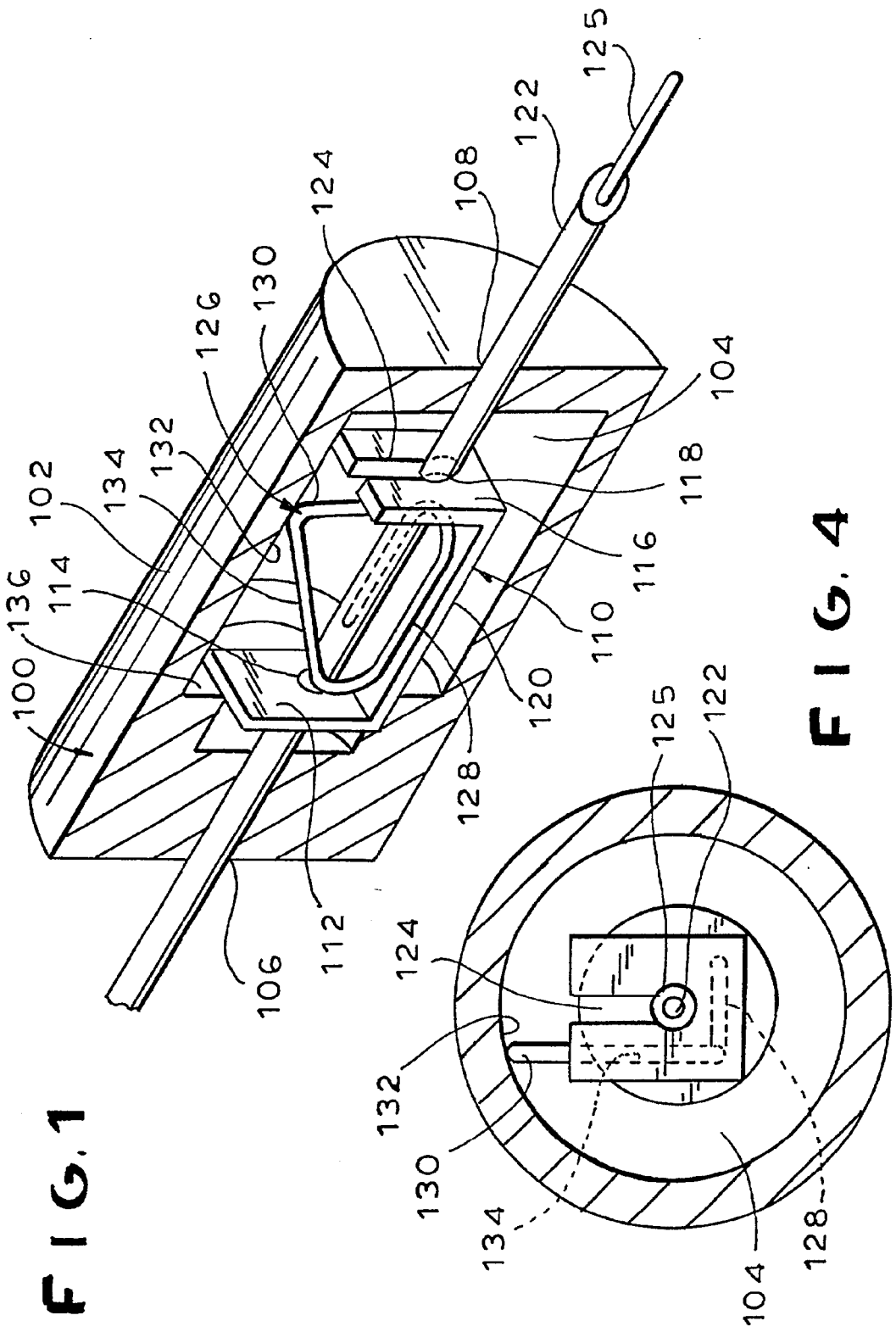

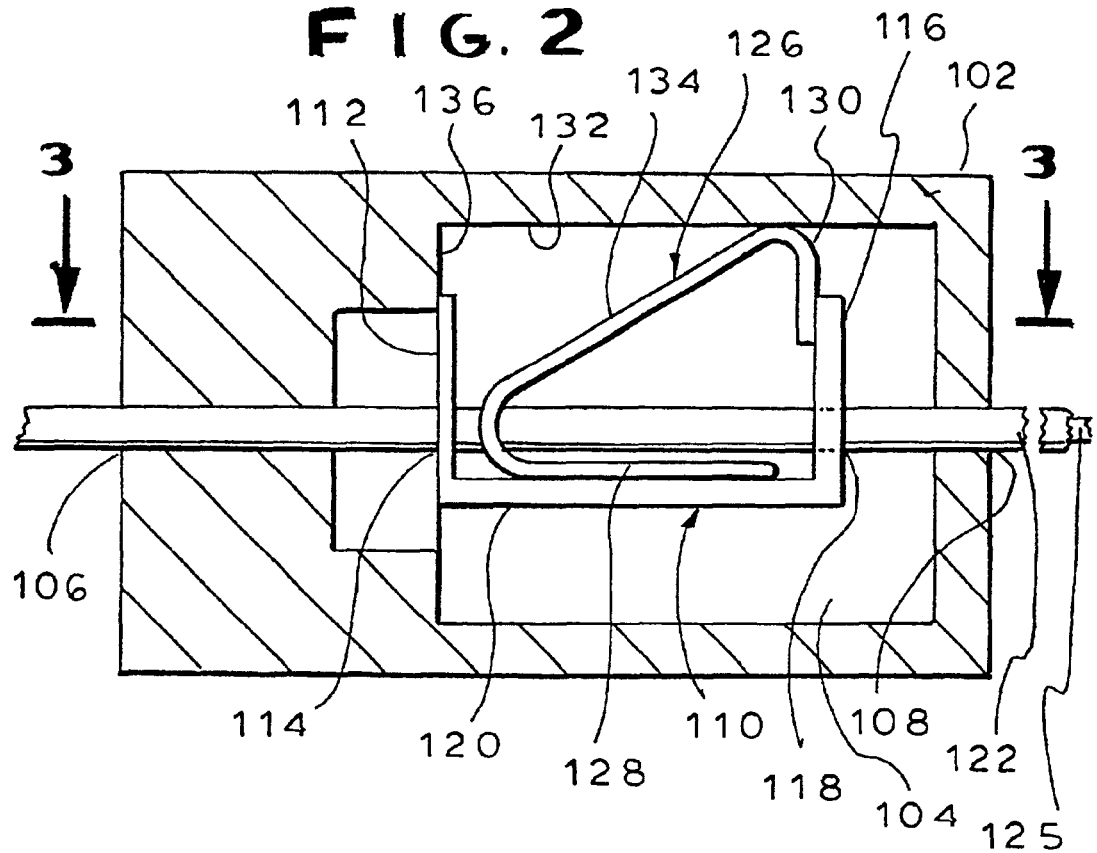

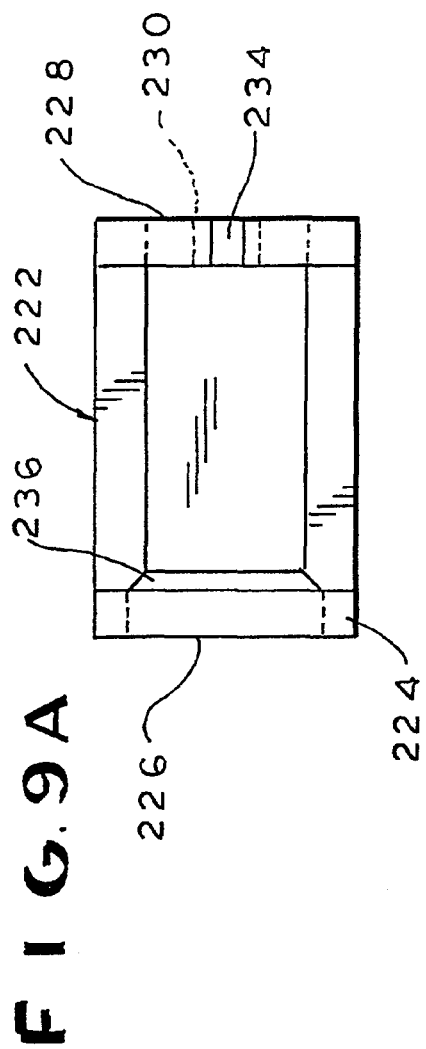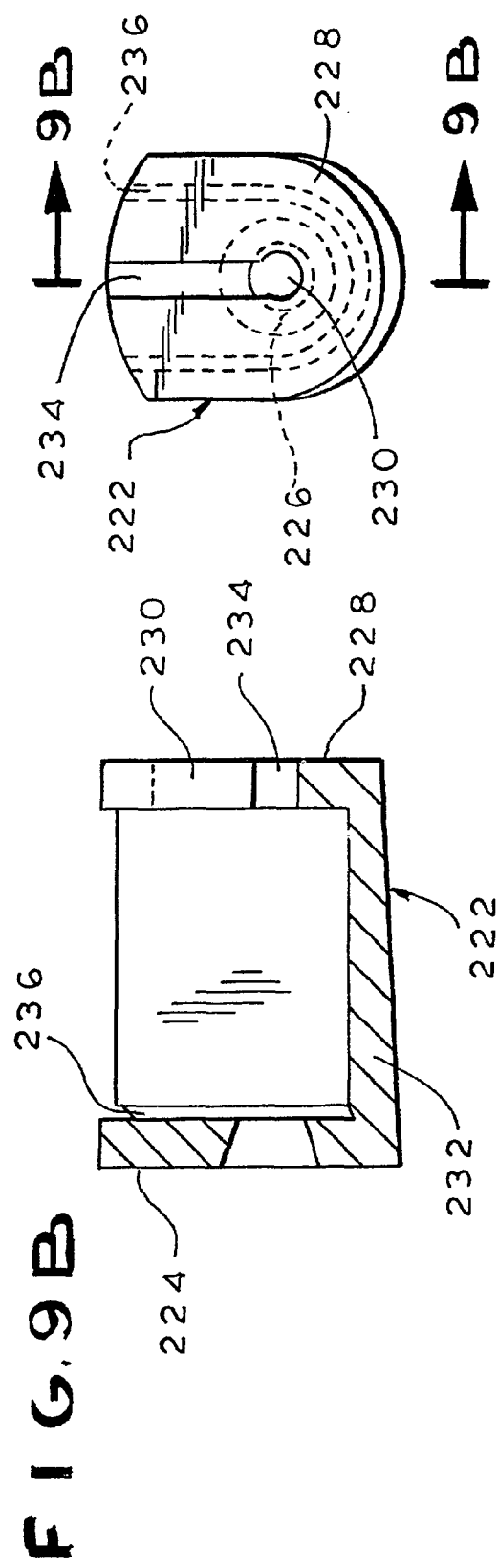

HYPODERMIC NEEDLE GUARD

CROSS REFERENCE TO RELATED APPLICATIONS

This application is a divisional of application Ser. No. 09/369,866 entitled HYPODERMIC NEEDLE GUARD, filed on Aug. 9, 1999, by William J. Voitasek, which was issued on Aug. 28, 2001, as U.S. Pat. No. 6,280,419. The present application is related to application Ser. No. 09/878, 012 entitled HYPODERMIC NEEDLE GUARD, filed on Jun. 8, 2001, by William J. Voitasek, which was issued on Nov. 26, 2002, as U.S. Pat. No. 6,485,468.

FIELD OF THE INVENTION

This invention relates generally to insuring the safe disposal of hypodermic needles. In particular, this invention relates to a device that is storable on the needle and that automatically locks over the end of the needle when the tip of the needle has been retracted within the interior of the device.

BACKGROUND OF THE INVENTION

The danger of infection from accidental contact with the tip of a used hypodermic needle has long been recognized and is well documented. In most procedures, the greatest avoidable risk of accidental needle puncture, also referred to as a "needlestick", occurs during handling of the used needle, when an operator generally inserts the used needle into a protective sheath for disposal. This action usually requires the operator to move the hand which holds the sheath toward the pointed tip of the needle, and any inaccuracy in this operation raises the possibility of a puncture. The risk of this is greatly increased if the operator is working under stress, such as time pressure or fatigue, or is handicapped by marginal eyesight or unsteady hands.

The problem of accidental needlesticks has recently engaged the attention of the United States Congress. The "Health Care Worker Needlestick Prevention Act" was recently introduced in both the House of Representatives and the Senate. The Act, if passed, would require the Secretary of Labor, acting through the Department of Labor's Occupational Safety and Health Administration, to amend OSHA's bloodborne pathogens standard to require that, among other things, employers utilize "engineered sharps injury protections." The Act generally defines "engineered sharps injury protections" as physical attributes that effectively reduce the risk of a needlestick injury and that are built into needle devices or other sharp, non-needle devices that are encountered in a health care setting.

A number of such "engineered sharps injury protections" have been developed for needle devices to deal with the general problem of needlesticks. One such device is disclosed in U.S. Pat. No. 5,322,517 to Sircom et al., entitled "Disposable Automatic Hypodermic Needle Guard" ("the Sircom Patent"). The Sircom Patent discloses several embodiments for a protecting device for covering the tip of a needle. The protecting device takes the form of a protective guard which is initially stored on the barrel of the needle and remote from its tip, and which is displaceable to a position enclosing the needle tip where it automatically locks in this position, serving as a protecting means for the needle tip. In the embodiment shown in FIGS. 35 through 39, a locking device includes a pivoting or lever arm or lever 101 of stiff material, formed in the general shape of a broad U of unequal proportions, with the longer vertical leg, referred to as the locking plate 102, provided with a hole 103 of slightly larger diameter than that of the needle shaft 1 sufficient to allow the locking plate 102 to "cant" on the needle 1, as shown in FIG. 39 of the Sircom Patent.

A helical compression spring 104 is contained in a largely compressed state in longitudinal cavity 105 within the guard body 106, with its free end 125 pressing against the locking plate 102 of the lever 101 and urging the level 101 axially against the sloping internal face 107 of body 106, making contact at pivot point 108. The turning moment of the spring force tends to rotate the level 101 in a counter-clockwise direction about the pivot point 108, but the shorter vertical leg 109 of the lever 101, referred to as the latching or locking leg, prevents rotation by making contact with the needle shaft 1 at point 110.

The slope of the face 107 in relation to the geometry of the lever 101 is chosen to develop a component of reaction force that acts at the pivot point 108 in a downward direction against the lever 101, equal and opposite to the upward reaction force against the lever at the point 110. This balancing of vertical forces against the lever 101 substantially removes any radial force between the needle shaft 1 and the walls of the hole 103 into lever 101, thereby reducing axial frictional drag between the needle shaft 1 and the lever 101 when moving the guard device axially along the needle shaft.

When the needle shaft 1 is withdrawn into the protective guard and passes the point of contact with the sensing end of the locking leg 109 of the lever or pivot arm 101, the lever 101 rotates in a counter-clockwise direction about the pivot point 108 under the urging of the spring 104, which rotates the locking plate 102 until further rotation is prevented by the axial misalignment of the hole 103 and the needle shaft 1.

A problem with the protective guard described in the Sircom Patent is its complexity. For example, the protective guard requires a critical geometry to ensure that the lever 101 locks on the needle shaft 1 when the needle shaft 1 is retracted into the protective guard. In establishing this critical geometry, care must be taken to ensure a particular relationship between the thickness 111 of the latch 101, the distance 112 between the pivot point 108 and the center of the needle shaft 1, the diameter of the hole 103, the diameter of the needle shaft 1, and the coefficient of friction between the latch 101 and the needle shaft 1.

Another problem with the protective guard described in the Sircom Patent is that the locking leg 109 of the lever 101 does not provide a mechanism whereby a wire guide can pass therethrough after the needle shaft 1 has been withdrawn into the protective guard. It is desirable to enable a wire guide to pass through the protective guard after the needle tip has been retracted into the protective guard so that the wire guide can facilitate the advancement of a catheter into the blood vessel of a patient.

SUMMARY OF THE INVENTION

The present invention is directed to an apparatus that satisfies the need for a needle guard that is easy to manufacture and that permits the passage of a wire guide therethrough even after the needle tip has been retracted into the interior of the needle guard.

A device for inhibiting unintentional contact with the tip of a needle that has features of the present invention includes a housing having an interior cavity. A portion of the needle extends through the cavity and the tip of the needle is located outside of the housing during use of the needle. A pivoting member is located within the cavity and defines a distal opening and a proximal opening. These openings are sized to allow the needle to pass through the openings in the pivoting member. The pivoting member is canted into locking engagement with the needle to prevent further movement of the needle when the needle tip is within the cavity and the needle is withdrawn from the distal opening of the pivoting member.

In accordance with another embodiment of the present invention, a device for inhibiting unintentional contact with the tip of a needle includes a housing having an interior cavity. A portion of the needle extends through the cavity and a tip of the needle is located outside of the housing during the use of the needle. A pivoting member is located within the cavity, and defines a distal opening and a proximal opening, both of which are sized to allow the needle to pass through the pivoting member. The pivoting member further defines a slot that communicates with the distal opening and has a dimension that is insufficient to permit passage of the needle therethrough. The pivoting member is canted into locking engagement with the needle to prevent further movement of the needle when the needle tip is within the cavity and the needle is withdrawn from the distal opening of the pivoting member.

In accordance with a further embodiment of the present invention, a device for inhibiting intentional contact with the tip of a needle includes a housing having an interior cavity. A portion of the needle extends through the cavity and a tip of the needle is located outside of the housing during use of the needle. A pivoting member is located within the cavity, and has a proximal wall with a proximal opening therein and a distal wall with a distal opening therein. The openings are sized to allow the needle to pass through the walls. The distal wall further defines a slot that communicates with the distal opening and has a dimension that is insufficient to permit passage of the needle therethrough. A spring is disposed in the interior cavity of the housing to cant the pivoting member about the proximal opening to prevent further movement of the needle when the needle tip is within the cavity and the needle is withdrawn from the distal opening of the distal wall.

In accordance with another embodiment of the present invention, a device for inhibiting unintentional contact with the tip of a needle includes a housing that has an interior cavity. A portion of the needle extends through the cavity and a tip of the needle is located outside of the housing during use of the needle. A pivoting member is located within the cavity. The pivoting member defines distal opening and proximal openings that are sized to allow the needle to pass through the openings in the pivoting member. A canting means cants the pivoting member about the needle when the needle tip is within the cavity and the needle is withdrawn from the distal opening of the pivoting member. In this position the canting means is in locking engagement with the needle to prevent further movement of the needle.

In accordance with yet another embodiment of the present invention, a device for inhibiting unintentional contact with the tip of a needle includes a housing that has an interior cavity. A portion of the needle extends through the cavity, and a tip of the needle is located outside of the housing during use of the needle. A pivoting member is located within the cavity and defines a distal and proximal openings that are sized to allow the needle to pass through the pivoting member. The pivoting member further defines a slot that communicates with the distal opening and has a dimension that is insufficient to permit the forward movement of the needle therethrough. A canting means cants the pivoting member about the needle when the needle tip is within the cavity and the needle is withdrawn from the distal opening of the pivoting member. In this position the canting means is in locking engagement with the needle to prevent further movement of the needle.

In accordance with yet another embodiment of the present invention, a device for inhibiting intentional contact with the tip of a needle includes a housing that has an interior cavity. A portion of the needle extends through the cavity, and a tip of the needle is located outside of the housing during use of the needle. A pivoting member is located within the cavity and has a proximal wall with a proximal opening therein and a distal wall with a distal opening therein. The proximal and distal openings are sized to allow the needle to pass through the proximal and distal walls. The distal wall further defines a slot that communicates with the distal opening and has a dimension that is insufficient to permit forward movement of the needle therethrough. A spring is disposed in the interior cavity of the housing and defines an opening for permitting the needle to pass therethrough. A portion of the spring is canted about the needle when the needle tip is within the cavity and the needle is withdrawn from the distal opening of the distal wall to bind the needle to prevent its further movement.

In accordance with a further embodiment of the present invention, a device for inhibiting intentional contact with the tip of a needle comprises a housing having an interior cavity. A portion of the needle extends through the cavity and a tip of the needle is located outside of the housing during use of the needle. A pivoting member is located within the cavity and has a proximal wall with a proximal opening therein and a distal wall with a distal opening therein. The openings are sized to allow the needle to pass through the walls. The distal wall further defines a slot that communicates with the distal opening and has a dimension that is insufficient to permit forward movement of the needle therethrough. A compressible member is at least partially disposed between the needle and the pivoting member and is compressed therebetween when the needle tip is located outside of the housing during use of the needle.

The above, and other features, aspects, and advantages of the present invention will become apparent from the following description read in conjunction with the accompanying drawings, in which like reference numerals designate the same elements.

BRIEF DESCRIPTION OF THE DRAWINGS

In the drawings:

FIG. 1 shows a perspective view of a full section of a device having the features of the present invention;

FIG. 2 shows a front elevational view of a full section of the device of FIG. 1;

FIG. 3 shows a top plan view of a full section of the device of FIG. 2 along the cutting plane line designated 3—3;

FIG. 4 shows a side elevational view of a full section of the device of FIG. 3 along the cutting plane line designated 4—4;

FIGS. 9A through 9C show a top plan view, a front elevational view of a full section, and a side elevational view, respectively, of a pivoting member of the device shown in FIGS. 8A and 8B;

DESCRIPTION OF THE PREFERRED EMBODIMENTS

Figure 5:
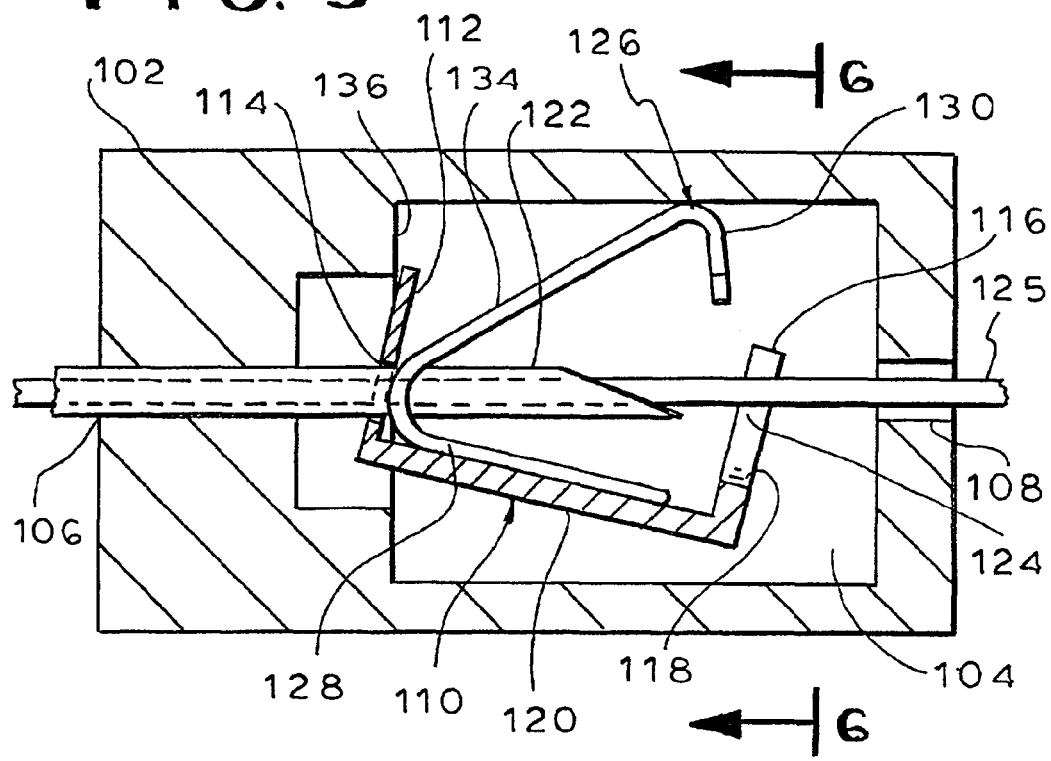
FIG. 5 shows a front elevational view of a full section of the device of FIG. 1 shown in its locked position.

FIGS. 1 through 6 show drawings of an embodiment of a needle guard device, generally designated 100, that has features of the present invention. A housing 102 of the needle guard device 100 has an interior cavity 104 defined therein. The housing 102 is formed with a proximal opening 106 at a proximal end thereof and a distal opening 108 at a distal end thereof.

A pivoting member, generally designated 110, is located within the interior cavity 104 of the housing 102. The pivoting member 110 has a proximal wall 112 that defines a proximal opening 114. The pivoting member 110 further comprises a distal wall 116 that defines a distal opening 118. The proximal and distal walls 112 and 116 are perpendicularly attached to a base 120 to form a U-shaped pivoting member 110. The pivoting member 110 is preferably formed from a hard metal material, like steel.

The openings 114 and 118 of the pivoting member 110 are sized to allow a needle 122 to pass therethrough. More specifically, the proximal opening 114 and the distal opening 118 are only slightly larger than the diameter of the needle 122 to permit the needle 122 to move through the openings 114 and 118. The proximal and distal openings 114 and 118 are preferably circular and coaxial.

The distal wall 116 further defines a slot 124 that communicates with the distal opening 118 and has a width that is smaller than the diameter of the distal opening 118 and the diameter of the needle 122. The width of the slot 124 is, however, large enough to permit a spring wire guide 125 to pass therethrough. The wire guide 125 is disposed within the lumen of the needle 122. The slot 124 preferably extends from the circumference of the distal opening 118 to an upper edge of the distal wall 116.

A spring, generally designated 126, has a U-shaped portion 128 disposed between the proximal and distal walls 112 and 116 and lying on an upper surface of the base 120 of the pivoting member 110. The spring 126 further has a rounded portion 130 that contacts an upper wall 132 of the interior cavity 104. An intermediate portion 134 of the spring 126 extends angularly upward to connect the U-shaped portion 128 to the rounded portion 130.

In operation, the needle 122 is inserted into the housing 102 through the proximal opening 106 and extends through the interior cavity 104, the proximal and distal openings 114 and 118 of the pivoting member 110, and the distal opening 108 of the housing 102, so that the tip of the needle 122 is located outside of the housing 102 during use of the needle 122. The spring 126 is compressed between the upper surface of the base 120 of the pivoting member 110 and the upper wall 132 of the interior cavity 104. As a result, the spring 126 biases the pivoting member 110 to cant about the needle 122.

Figure 6:
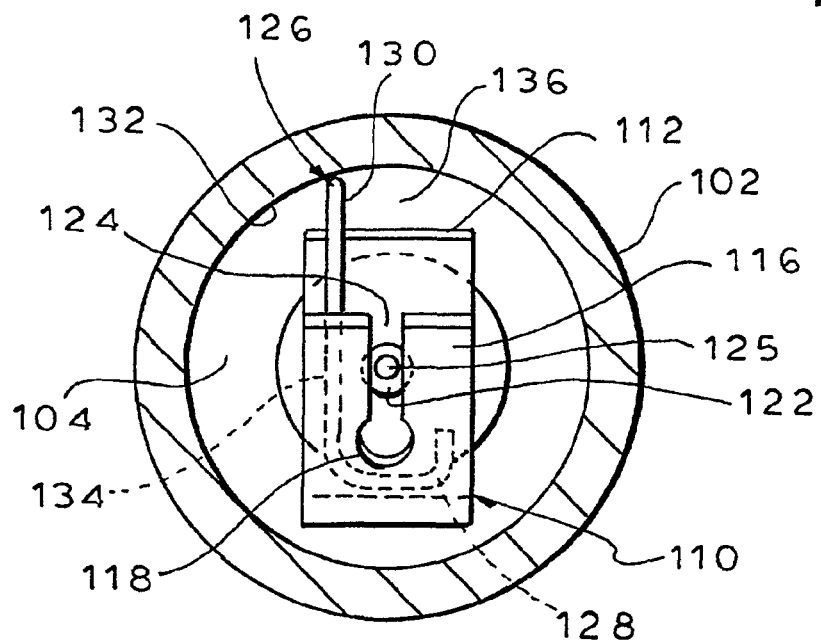
FIG. 6 shows a side elevational view of a full section of the device of FIG. 5 along the cutting plane line designated 6—6.

Referring to FIGS. 5 and 6, when the needle 122 is withdrawn into the housing 102 and, further, from the distal opening 118 of the pivoting member 110, the spring 126 moves toward, but does not attain, its uncompressed position, thereby causing the pivoting member 110 to cant about the needle 122. The proximal wall 112 thus becomes canted about the needle 122. Since the proximal wall 112 is preferably formed from a hard metal material and the proximal opening 114 thereof has a diameter that is only slightly larger than the diameter of the needle 122, the proximal wall 112 of the pivoting member 110 bites into the needle 122 to bind or lock the needle 122 to prevent its further forward or rearward movement. The hard metal material from which the pivoting member 110 is formed must thus provide an edge that is sufficiently sharp that the proximal wall 112 will indeed bite into the needle 122. The spring 126 thus provides a means for canting the pivoting member 110 into locking engagement with the needle 122 to prevent further movement of the needle 122 when its tip is within the interior cavity 104 and the needle 122 is withdrawn from the distal opening 118 of the pivoting member 110.

Any additional force applied to the needle 122 results in even more binding force being applied on the needle 122. For example, as best seen in FIG. 5, any attempt to withdraw the needle 122 from the needle guard device 100 causes the proximal wall 112 to contact an inner wall 136 of the interior cavity 104. The pivoting member 110 is thus pivoted about the point of contact between the proximal wall 112 and the inner wall 136 to reinforce the canting of the pivoting member 110, thereby further binding or locking the needle 122 to prevent its further movement. Therefore, once the pivoting member 110 has become canted about the needle 122, further rearward movement of the needle 122 is prevented.

In addition, further forward movement of the needle 122 is also prevented once the pivoting member 110 has become canted about the needle 122. The spring 126 maintains the pivoting member 110 in its canted position with respect to the needle 122. As a result, any attempt to push the needle 122 forward causes both the needle 122 and the pivoting member 110 to move forward together. In other words, there can be no relative movement between the tip of the needle 122 and the pivoting member 110 once the pivoting member 110 becomes canted about the needle 122. Therefore, once the distal wall 116 is pushed up against the housing 102, neither the pivoting member 110 nor the needle 122 can move forward.

If the binding force of the pivoting member 110 on the needle 122 could somehow be overcome—e.g., due to a failure of the proximal wall 112 of the pivoting member 110 to bite into the needle 122 or due to a failure of the spring 126—so that relative motion between the tip of the needle 122 and the pivoting member does somehow become possible, the forward movement of the needle 122 is blocked by the slot 124 of the pivoting member 110. As best seen in FIGS. 5 and 6, the tip of the needle 122 becomes generally aligned with the slot 124 once the spring 126 has expanded. Since the slot 124 has a width that is smaller than the diameter of the needle 122, movement of the needle 122 through the slot 124 is prevented and the tip of the needle 122 cannot be pushed from the device 100. The wire guide 125 that is disposed within the lumen of the needle 122 can, however, pass through the slot 124 because the slot 124 has a width that is greater than the diameter of the wire guide 125 to pass therethrough. Thus, the spring 126 positions the slot 124 to permit the wire guide 125 to exit the housing 102 even when the pivoting member 110 is canted about the needle 122.

Figure 7:
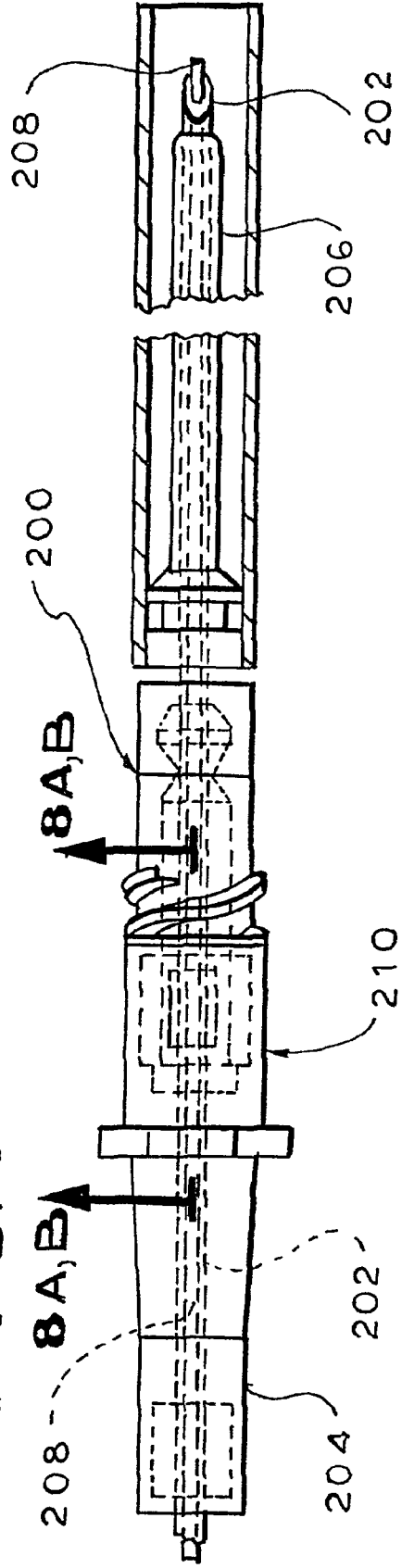
FIG. 7 shows a front elevational view of a catheter assembly that incorporates a device having the features of the present invention.

In a presently preferred embodiment, a device that has the features of the present invention is advantageously and effectively utilized in combination with a catheter assembly. An exemplary catheter assembly, generally designated 200, is shown in FIG. 7. A needle 202 is joined at the end opposite its tip to a hub 204. A catheter 206 is sized to be telescopically fitted over the needle 202. The catheter 206 is slightly shorter than the needle 202 so that, when the catheter 206 is pushed fully back toward the needle hub 204, the tip of the needle 202 projects outwardly from the catheter 206 by an amount sufficient to permit puncture of a patient's skin and blood vessel by the user of the catheter assembly 200. A spring wire guide 208 extends through the lumen of the needle 202 and outwardly from its tip into and through the lumen of the patient's blood vessel. In use, the distal end of the wire guide 208 is extended into the blood vessel for a distance that is approximately equal to the length of the catheter 206.

Figure 8A:
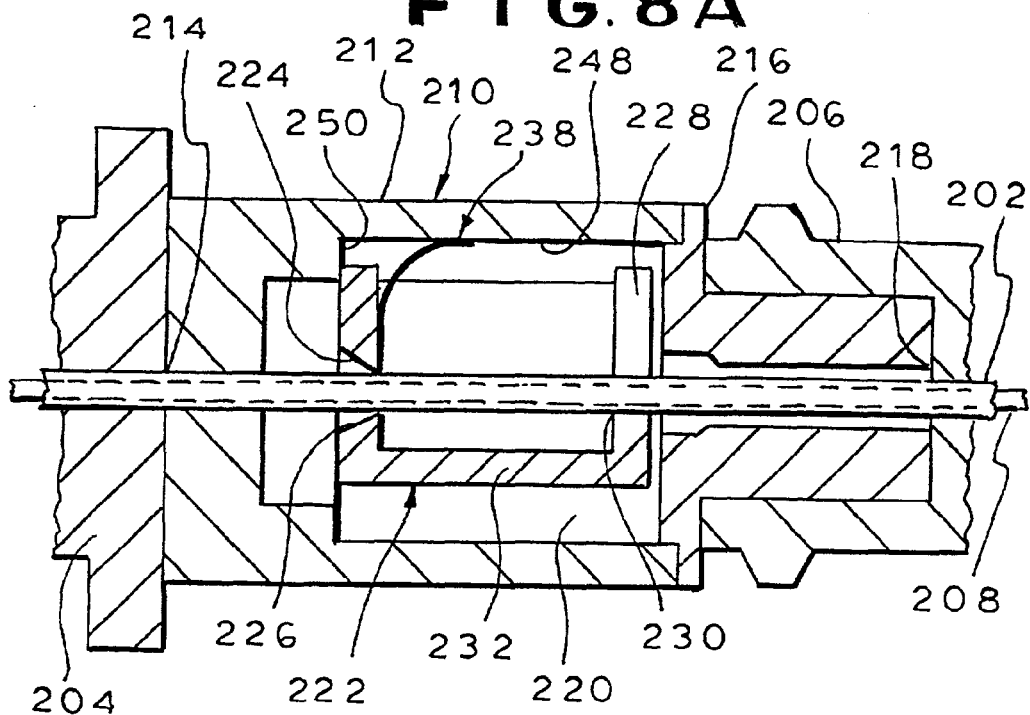
FIG. 8A shows a front elevational view of a partial section of the catheter assembly of FIG. 7 along the cutting line designated by the cutting plane line 8A,B—8A,B.

As shown in FIG. 8A, a device that has the features of the present invention is advantageously interposed between the needle hub 204 and the proximal end of the catheter 206 shown in FIG. 7. The device, generally designated 210, includes a cylindrical housing body 212 that is formed with a proximal opening 214 at a proximal end thereof. The needle guard device 210 further includes a housing cap 216 that is formed with a distal opening 218 at a distal end thereof. The housing body 212 and the housing cap 216 are preferably molded from a plastic material. The housing cap 216 is secured to the housing body 212 using a glue, a solvent, or some other conventional adhesive that is well-known to those having ordinary skill in the art. Once secured together, the housing body 212 and the housing cap 216 define an interior cavity 220.

A pivoting member, generally designated 222, is located within the interior cavity 220, and is shown in more detail in FIGS. 9A through 9C. The pivoting member 222 has a proximal wall 224 that defines a beveled proximal opening 226, and a distal wall 228 that defines a distal opening 230. The proximal and distal walls 224 and 228 are located at opposite sides of a rounded, U-shaped member 232 to form the pivoting member 222. The pivoting member 222 is preferably molded as one piece from a plastic material.

The proximal opening 226 and the distal opening 230 of the pivoting member 222 are sized to allow the needle 202 to pass through the openings 226 and 230. More specifically, the proximal and distal openings 226 and 230 are only slightly larger than the diameter of the needle 202 to permit the needle 202 to move through the openings 226 and 230. The proximal and distal openings 226 and 230 are preferably circular and coaxial.

The distal wall 228 of the pivoting member 222 further defines a slot 234 that communicates with the distal opening 230 and has a width that is smaller than the diameter of the distal opening 230 and the diameter of the needle 202. The width of the slot 234 is, however, large enough to permit the wire guide 208 to pass therethrough. The slot 234 preferably extends from the circumference of the distal opening 230 to an upper edge of the distal wall 228.

Figure 10:
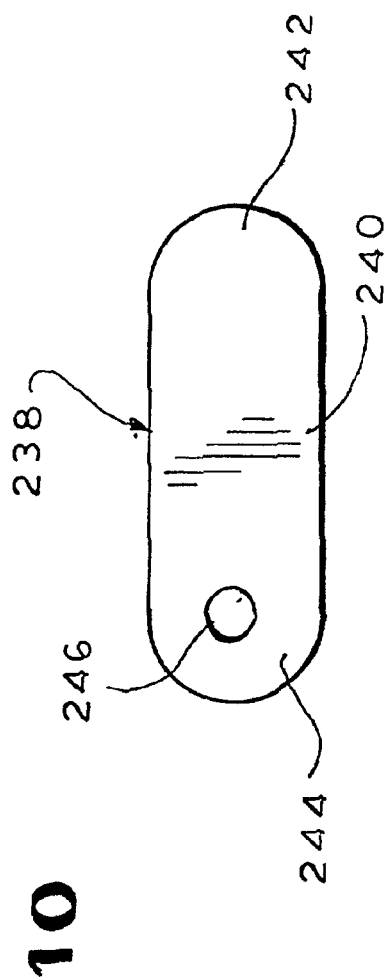
FIG. 10 shows a canting means of the device shown in FIGS. 8A and 8B.

The proximal end of the U-shaped member 232 has edges that are beveled, preferably at a 45° angle, to define a longitudinally extending, open-ended groove 236 which is configured and dimensioned to receive and to hold one end of a spring, generally designated 238. As best seen in FIG. 8A, the locking spring 238 is at least partially disposed in the groove 236. As shown in FIG. 10, the locking spring 238 has a substantially rectangular center portion 240 and substantially semi-circular end portions 242 and 244 located at opposite ends of the center portion 240. The end portion 244 of the locking spring 238 defines an opening 246. The locking spring 238 is inserted into the groove 236 so that the opening 246 of the locking spring 238 is generally aligned with the proximal opening 226 of the pivoting member 222 to allow the needle 202 to pass through the two openings 226 and 246. The opening 246 preferably has a diameter that is only slightly larger than the diameter of the needle 202. The locking spring 238 is preferably formed from a resilient material that is nonetheless hard enough, and can provide an edge that is sharp enough, to bite into the needle 202. In the presently preferred embodiment, the locking spring 238 is formed from stainless spring steel and has a thickness that is not less than approximately 0.003 inches.

As best seen in FIG. 8A, in operation the needle 202 is inserted into the housing body 212 through its proximal opening 214 and extends through the interior cavity 220, the proximal and distal openings 226 and 230 of the pivoting member 222, and the distal opening 218 of the housing cap 216, so that the tip of the needle 202 is located outside of the housing cap 216 during use of the catheter assembly. The locking spring 238 is bent from its normally straight position toward an L-shaped position. The end portion 242 of the spring 240 is in contact with the upper wall 248 of the interior cavity 220. The other end portion 244 of the spring 240 is disposed in the groove 236 such that the opening 246 of the end portion 244 is generally aligned with the proximal opening 226 of the proximal wall 224. The locking spring 238 biases the pivoting member 222 to be canted about the needle 202.

When the needle 202 is withdrawn into the housing body 212 and, further, from the distal opening 230 of the pivoting member 222, the locking spring 238 moves toward a non-bent position, thereby causing the pivoting member 222 to cant about the needle 202. The portion of the locking spring 238 that is disposed in the groove 236 of the pivoting member 222 thus becomes canted about the needle 202. Since the locking spring 238 is formed from a sufficiently hard metal material, such as stainless spring steel, and the diameter of the opening 246 of the locking spring 238 is only slightly larger than the diameter of the needle 202, the locking spring 238 bites into the needle 202 to bind or lock the needle 202 to prevent its further forward or rearward movement when the pivoting member 222 is canted about the needle 202 after the tip of the needle 202 is withdrawn into the interior cavity 220 and from the distal opening 230 of the pivoting member. The locking spring 238 thus provides a means for canting the pivoting member about the needle when the needle tip is within the cavity and the needle is withdrawn from the distal opening of the pivoting member. The canting means further engages the needle to prevent the removal of the needle from the housing.

Any additional force applied to the needle 202 results in even more binding force being applied on the needle 202.

Figure 8B:
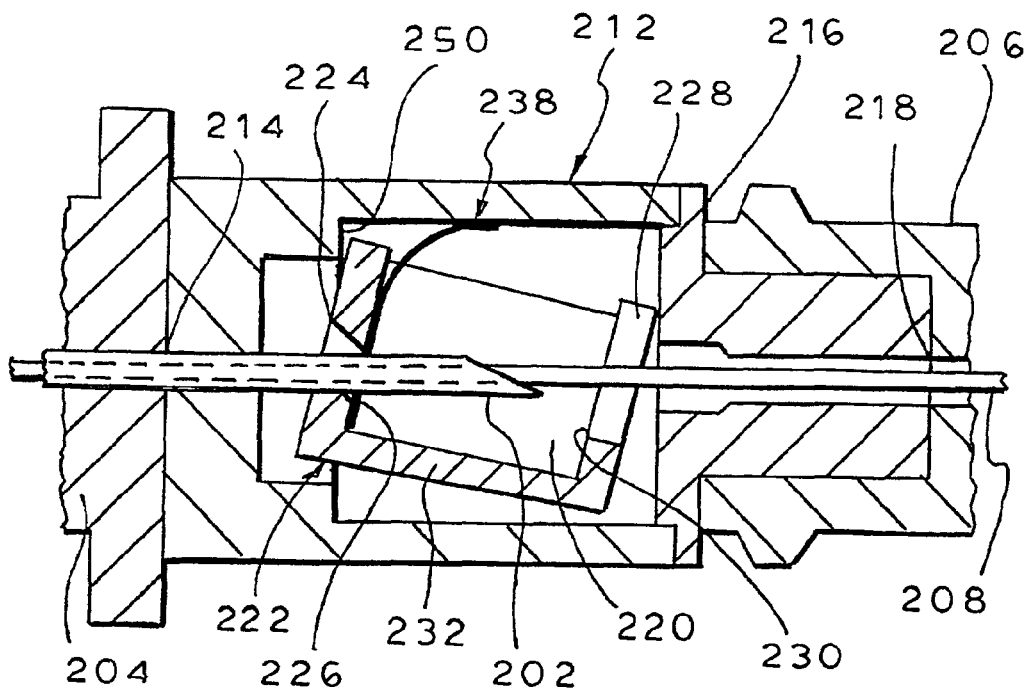
FIG. 8B shows a front elevational view of a partial section of the catheter assembly of FIG. 7 along the cutting line designated by the cutting plane line 8A,B—8A,B showing the device of the present invention in its locked position.
Figure 11:
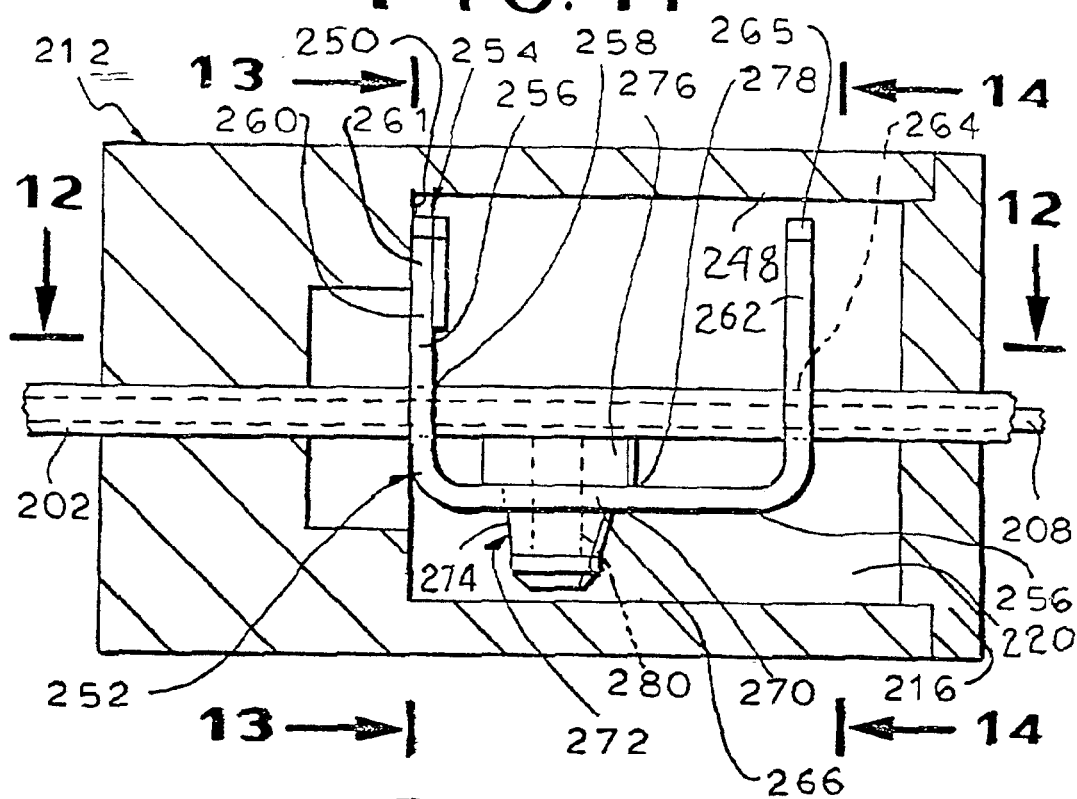
FIG. 11 shows the device of FIG. 8A with another embodiment of the pivoting member.
Figure 12:
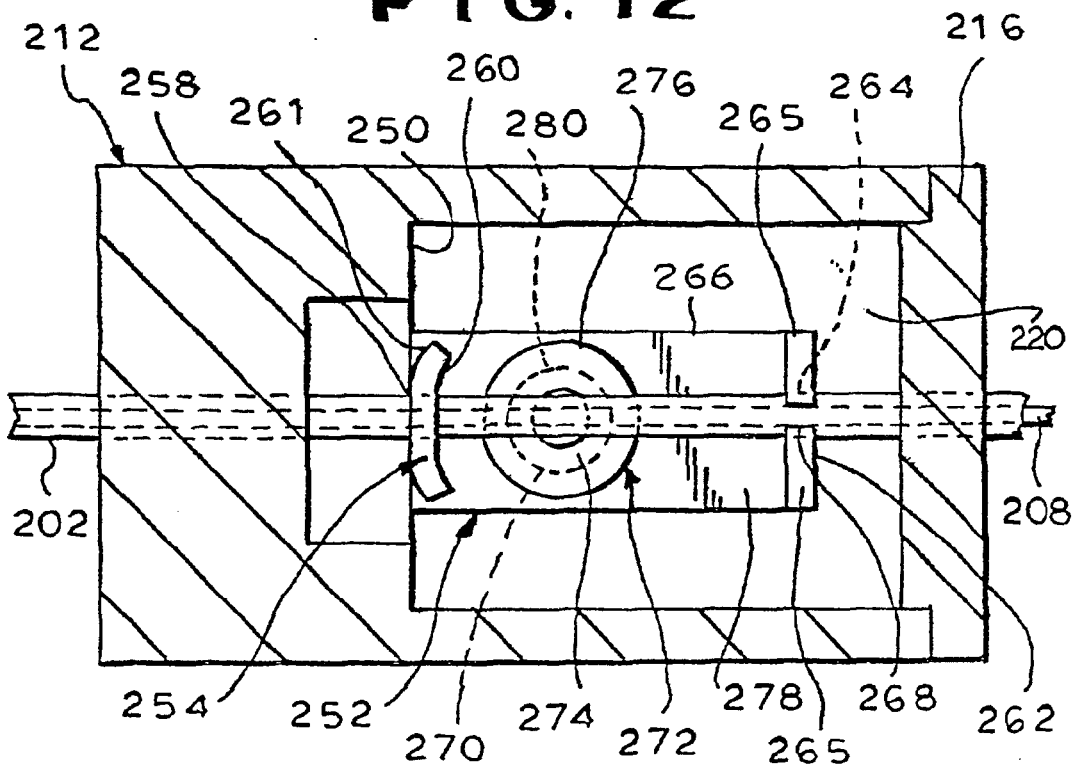
FIG. 12 shows a top plan view of the device of FIG. 11 along the cutting plane line 12—12.

For example, as best seen in FIG. 8B, any attempt to withdraw the needle 202 from the needle guard device 210 causes the proximal wall 224 of the pivoting member 222 to contact a back wall 250 of the interior cavity 220. The pivoting member 222 is thus pivoted about the point of contact between the proximal wall 224 and the back wall 250 to reinforce the canting of the pivoting member 222. As a result, the locking spring 238 further bites into the needle 202 to increasingly bind or lock the needle 202 to prevent its further movement. Therefore, once the pivoting member 222 has become canted about the needle 202, further rearward movement of the needle 202 is prevented.

In addition, further forward movement of the needle 202 is also prevented once the pivoting member 222 has become canted about the needle 202. The locking spring 238 maintains the pivoting member 222 in its canted position with respect to the needle 202. As a result, any attempt to push the needle 202 forward causes both the needle 202 and the pivoting member 222 to move forward together. In other words, there can be no relative movement between the tip of the needle 202 and the pivoting member 222 once the pivoting member 222 becomes canted about the needle 202. Therefore, once the distal wall 228 of the pivoting member 222 is pushed against the housing cap 216, neither the pivoting member 222 nor the needle 202 can move further.

If the binding force of the pivoting member 222 on the needle 202 could somehow be overcome—e.g., due to a failure of the locking spring 238 to bite sufficiently into the needle 202—so that relative motion between the tip of the needle 202 and the pivoting member does somehow become possible, the forward movement of the needle 202 is blocked by the slot 234 of the pivoting member 222. As best seen in FIG. 8B, the tip of the needle 202 becomes generally aligned with the slot 234 once the locking spring 238 has expanded. Since the slot 234 has a width that is smaller than the diameter of the needle 202, movement of the needle 202 is prevented and the tip of the needle 202 cannot be pushed from the device 210. The wire guide 208 that is disposed within the lumen of the needle 202 can, however, pass through the slot 234 because the slot 234 has a width that is larger than the diameter of the wire guide 208. Thus, the locking spring 238 positions the slot 234 to permit the wire guide 208 to exit the housing cap 216 even when the pivoting member 222 is canted about the needle 202.

In a presently preferred embodiment, a pivoting member of the type shown in FIGS. 11–15 is located within the interior cavity 220 that is defined by the housing body 212 and the housing cap 216. The pivoting member, generally designated 252, includes a proximal wall, generally designated 254, that has a substantially rectangular portion 256 with a proximal opening 258 defined therein. Integrally formed with the rectangular portion is a rounded portion 260 that sits atop the rectangular portion 256. The rounded portion 260 preferably has a rounded edge 261. The pivoting member 252 further comprises a distal wall 262 that defines a distal opening 264. The proximal and distal walls 254 and 262 are perpendicularly attached to a base 266 to form the U-shaped pivoting member 252. The pivoting member 252 is preferably formed from a metal material, such as steel, by a punching operation.

The distal wall 262 further defines a slot 268 that communicates with the distal opening 264 and has a width that is smaller than the diameter of the distal opening 264 and the diameter of the needle 202. The width of the slot 268 is, however, large enough to permit the spring wire guide 208 to pass therethrough. The wire guide 208 is disposed within the lumen of the needle 202. The slot 268 preferably extends from the circumference of the distal opening 264 to an upper edge 265 of the distal wall 262. The upper edge 265 of the distal wall 262 is preferably rounded.

The base 266 of the pivoting member 252 has an opening 270 defined therein to permit a compressible member, generally designated 272, to be at least partially inserted therein. The compressible member 272 has a body portion 274 that is at least partially disposed within the opening 270 and that fits snugly therein. The compressible member 272 further has a head portion 276 that is integrally formed with the body portion 274. The head portion 276 is sized so that it rests on a surface 278 of the base 266 and thus cannot be inserted in the opening 270. The compressible member 272 is thus at least partially disposed between the needle 202 and the pivoting member 252, and it is compressed therebetween when the tip of the needle 202 is located outside of the housing body 212 during use of the needle 202. A channel 280 extends longitudinally through the compressible member 272. The compressible member 272 is preferably made from a rubber or plastic material that is characterized by a durometer measurement that is on the order of approximately 80A.

The pivoting member 252 operates in a manner similar to the pivoting member 222, except as described herein. In the pivoting member 222, as shown in FIG. 8A, the locking spring 238 biases the pivoting member 222 to be canted about the needle 202. In contrast, in the pivoting member 252 shown in FIGS. 11–15, the compressible member 272 biases the pivoting member 252 to be canted about the needle 202. When the needle 202 is inserted into the pivoting member 252 through both the proximal opening 258 and the distal opening 264, the head portion 276 of the compressible member 272 is compressed to provide the spring force necessary to bias the pivoting member 252 to be canted about the needle 202. When the needle 202 is withdrawn into the housing body 212 and, further, from the distal opening 264 of the pivoting member 252, the head portion 276 of the compressible member 272 moves toward an uncompressed position, thereby causing the pivoting member 252 to cant about the needle 202.

Figure 13:
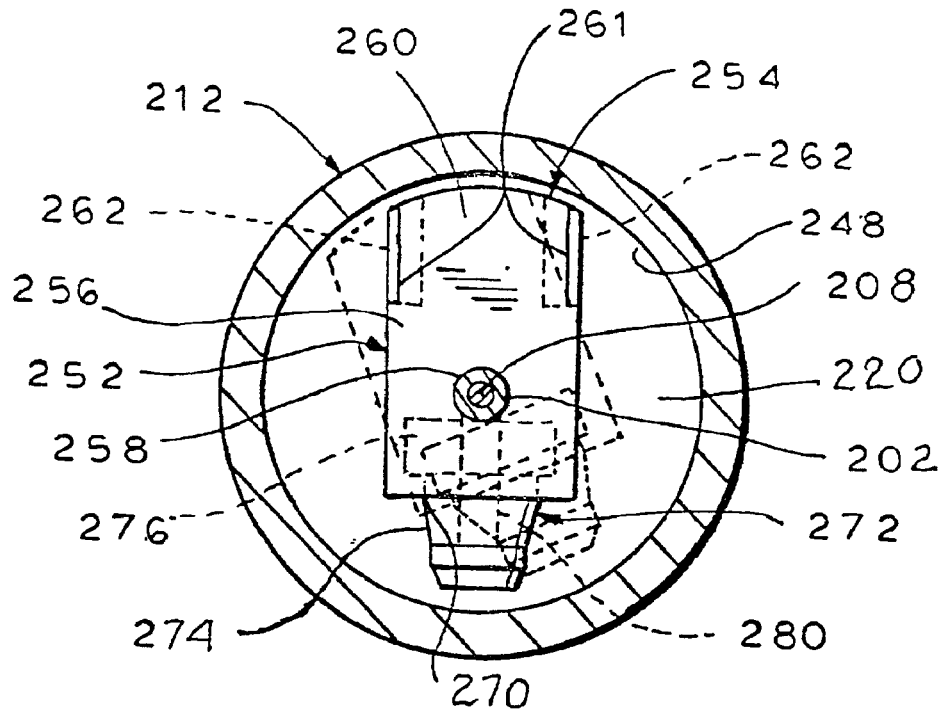
FIG. 13 shows a side elevational view of the device of FIG. 11 along the cutting plane line 13—13.
Figure 14:
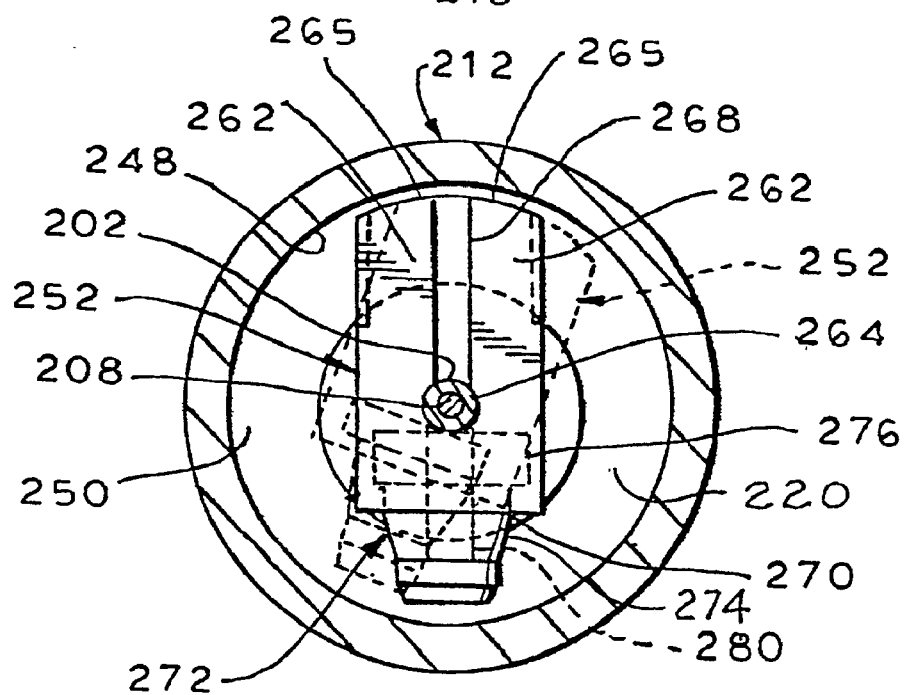
FIG. 14 shows a side elevational view of the device of FIG. 11 along the cutting plane line 14—14.
Figure 15:
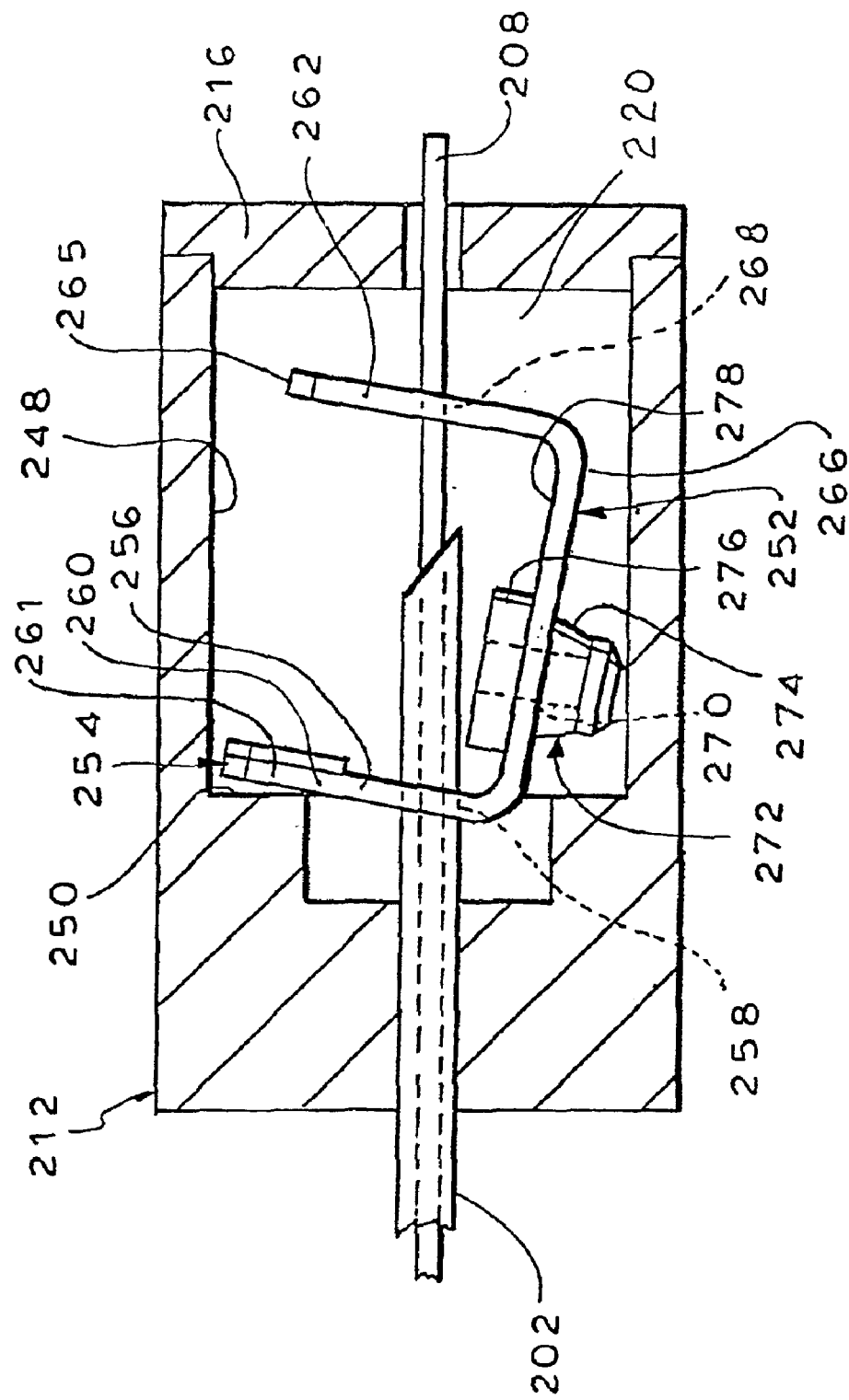
FIG. 15 shows the device of FIG. 11 in its locked position.

The rounded edge 261 of the rounded portion 260 of the proximal wall 254 advantageously prevents the needle 202 from being accidentally removed from the housing body 212. If the pivoting member 252 is made from a hard, metal material like steel and has proximal and distal walls that are entirely substantially rectangular, so that their upper edges are flat; and if the housing body 212 is formed using a plastic material, the possibility exists that the corners of the edges of the proximal wall could bite into the back wall 250 of the interior cavity 220, thereby immobilizing the pivoting member 252. As a result, a user who manipulated the needle 202 while holding the housing body 212 could conceivably remove the needle 202 from the housing body 212. The rounded edge 261 of the rounded portion 260 of the proximal wall 254 precludes such an occurrence. As best seen in FIGS. 13 and 14, the rounded edge 261 prevents the proximal wall 254 from biting into the back wall 250 by permitting the proximal wall 254 to rotate within the interior cavity 220 as the needle 202 is being manipulated by the user.

The embodiments of the present invention that have been described herein have many advantages, including simplicity and reliability of operation, ease of manufacture, and the ability to permit a wire guide to extend through the needle guard device even when the tip of the needle is retracted into and locked within the interior of the needle guard device. The action of the spring in the first embodiment to cause the proximal wall of the pivoting member to bite into the needle when the tip of the needle is pulled through the distal opening of the pivoting member provides a simple mechanism for binding or locking the needle within the needle guard device when the needle is withdrawn from the distal opening of the pivoting member. The action of the spring itself to bite into the needle in the second embodiment provides an elegant mechanism for applying a binding or locking force to the needle once it is drawn into the needle guard device. Finally, the replacement of the spring in the second embodiment with the compressible member provides an elegant mechanism for biasing the pivoting member to cant about the needle. The simplicity of operation of the described embodiments of the present invention enables the embodiments to be manufactured easily, reliably, and inexpensively.

The embodiments of the present invention that have been described herein include the further advantage that a wire guide can extend through the needle guard device even when the needle is locked within the interior of the needle guard device. This is possible because the general alignment of the slot of the distal wall of the pivoting member in both embodiments permits the spring wire guide to extend through the needle guard device while simultaneously preventing the needle from exiting the needle guard device.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A device for inhibiting unintentional contact with the tip of a needle, said device comprising:
   a housing having an interior cavity, a portion of said needle extending through said cavity and a tip of said needle located outside of said housing during use of said needle;
   a pivoting member located within said cavity, said pivoting member defining a distal opening and a proximal opening, said openings sized to allow said needle to pass through said openings in said pivoting member; and
   means for canting said pivoting member into locking engagement with said needle to prevent removal of said needle from said housing when said needle tip is within said cavity and said needle is withdrawn from said distal opening of said pivoting member.

2. The device of claim 1, wherein said openings are slightly larger than the diameter of said needle to permit said needle to move through said openings when said pivoting member is not canted.

3. The device of claim 2, wherein said pivoting member comprises a U-shaped member having a proximal wall that defines said proximal opening and a distal wall that defines said distal opening.

4. The device of claim 3, wherein said pivoting member further defines a slot communicating with said distal opening, said slot having a dimension that is smaller than said distal opening.

5. The device of claim 4, wherein said slot extends to an upper edge of said distal wall.

6. The device of claim 3, wherein said canting means causes said proximal wall to cant about said needle when said needle is withdrawn from said distal opening of said pivoting member.

7. The device of claim 6, wherein said proximal wall binds said needle to prevent further movement of said needle.

8. The device of claim 7, wherein said canting means comprises a spring disposed within said interior cavity of said housing to bias said pivoting member to cant about said needle.

9. The device of claim 8, wherein said needle and said device are used in combination with a catheter.

10. The device of claim 9, wherein said device is attached at a proximal end of said catheter.

11. A device for inhibiting unintentional contact with the tip of a needle, said device comprising:
    a housing having an interior cavity, a portion of said needle extending through said cavity and a tip of said needle located outside of said housing during use of said needle;
    a pivoting member located within said cavity, said pivoting member defining a distal opening and a proximal opening, said openings sized to allow said needle to pass through said pivoting member;
    said pivoting member further defining a slot communicating with said distal opening and having a dimension that is insufficient to permit forward movement of said needle therethrough; and
    means for canting said pivoting member into locking engagement with said needle to prevent removal of said needle from said housing when said needle tip is within said cavity and said needle is withdrawn from said distal opening of said pivoting member.

12. The device of claim 11, wherein said needle further comprises a wire guide in a lumen thereof and said slot has a dimension that is sufficient to allow said wire guide to pass therethrough.

13. The device of claim 12, wherein said canting means causes said pivoting member to cant about said needle when said needle is withdrawn from said distal opening of said pivoting member.

14. The device of claim 13, wherein said canting means positions said slot to permit said wire guide to exit said housing when said pivoting member is canted.

15. The device of claim 14, wherein said canting means comprises a spring disposed within said interior cavity of said housing to bias said pivoting member to cant about said needle.

16. A device for inhibiting intentional contact with the tip of a needle, said device comprising:
    a housing having an interior cavity, a portion of said needle extending through said cavity and a tip of said needle located outside of said housing during use of said needle;
    a pivoting member located within said cavity, said pivoting member having a proximal wall with a proximal opening therein and a distal wall with a distal opening therein, said openings sized to allow said needle to pass through said walls;
    said distal wall further defining a slot communicating with said distal opening and having a dimension that is insufficient to permit forward movement of said needle therethrough; and
    a spring disposed in said interior cavity of said housing to cant said proximal wall about said needle to prevent further movement of said needle when said needle tip is within said cavity and said needle is withdrawn from said distal opening of said distal wall.

17. The device of claim 16, wherein the diameters of said openings are slightly larger than the diameter of said needle to permit said needle to move through said openings when said pivoting member is not canted.

18. The device of claim 17, wherein said openings are circular and coaxial.

19. The device of claim 16, wherein said proximal and distal walls are perpendicularly attached to a base wall to form a U-shaped pivoting member.

* * * * *